United States Patent [19]

Winter et al.

[11] Patent Number: 5,278,314

[45] Date of Patent: Jan. 11, 1994

[54] 5-THIO-SUBSTITUTED BENZOTRIAZOLE UV-ABSORBERS

[75] Inventors: Roland A. E. Winter, Armonk; Volker H. von Ahn, Mahopac, both of N.Y.; Tyler A. Stevenson, Teaneck, N.J.; Mark S. Holt, West Nyack; Ramanathan Ravichandran, Nanuet, both of N.Y.

[73] Assignee: Ciba-Geigy Corporation, Ardsley, N.Y.

[21] Appl. No.: 828,290

[22] Filed: Feb. 5, 1992

Related U.S. Application Data

[63] Continuation-in-part of Ser. No. 654,156, Feb. 12, 1991, abandoned.

[51] Int. Cl.⁵ .......................................... C07D 249/20
[52] U.S. Cl. .................................................. 548/259
[58] Field of Search .......................................... 548/259

[56] References Cited

U.S. PATENT DOCUMENTS 3,004,896 10/1961 Heller et al. ............................ 167/90
3,189,615  6/1965 Heller et al. ............................ 260/308
3,766,205 10/1973 Heller et al. ...................... 260/308 B

FOREIGN PATENT DOCUMENTS 0323853 7/1989 European Pat. Off. .

Primary Examiner—Patricia L. Morris
Attorney, Agent, or Firm—Luther A. R. Hall

[57] ABSTRACT 2-(2-Hydroxyphenyl)-2H-benzotriazole UV-absorbers substituted at the 5-position of the benzo ring by a thioether group exhibit enhanced absorption in the near visible range (over 350 nm) allowing said compounds to be particularly effective in protecting polymer systems which are prone to degradation caused by actinic irradiation with wavelengths over 350 nm.

4 Claims, No Drawings

5-THIO-SUBSTITUTED BENZOTRIAZOLE UV-ABSORBERS

This is a continuation-in-part of application Ser. No. 654,156, filed on Feb. 12, 1991, now abandoned.

The instant invention pertains to 2-(2-hydroxyphenyl)-2H-benzotriazole compounds substituted in the 5-position of the benzo ring by a thioether moiety and to stabilized compositions containing said compounds.

BACKGROUND OF THE INVENTION

The 2-(2-hydroxyphenyl)-2H-benzotriazoles represent a very important class of commercial UV-absorbers which have found wide-spread acceptance as stabilizers for protecting a host of organic substrates against the deleterious effects of exposure to actinic radiation.

With such a long period of commercial and technical interest in this class of compounds, there are a host of publications and patents describing this general class of compounds. Few of these references recite substitution of 2H-benzotriazoles with any group containing sulfur, let alone with a thioether moiety.

European Patent Application No. 323,853, pertaining to the stabilization of color photographic material, discloses generically 2H-benzotriazole compounds which may be substituted on the benzo ring, on the phenyl ring or on both rings by a host of possible substituents including inter alia alkylthio or arylthio moieties. Only 5-methylthio-2-(2-hydroxy-3-sec-butyl-5-tert-butylphenyl)-2H-benzotriazole is specifically named. This reference defines the benzotriazoles very broadly without exemplification of compounds containing 5-alkylthio or 5-arylthio substitution, and it does not point out the beneficial stabilization properties obtained when an alkylthio or arylthio moiety is located on the 5-position of the benzo ring.

U.S. Pat. No. 3,766,205 describes 5-mercapto-2-(2-hydroxy-3,5-dimethylphenyl)-2H-benzotriazole and the ester prepared by the Michael addition of said mercaptan to ethyl acrylate. The instant compounds are structurally distinguished from the Michael adducts of this reference. The prior art Michael adducts are subject to thermal retro Michael cleavage to eliminate the acrylate group. Such compounds would be expected to have lower thermal stability than the instant compounds.

The instant compounds and compositions are distinguished from the compounds of the prior art. None of these references disclose that substitution of a 2H-benzotriazole compound in the 5-position of the benzo ring by an alkylthio, arylthio or aralkylthio moiety results in a significant increase in UV absorbance and also shifts the absorption maximum by about 20 nm toward longer wavelength relative to benzotriazoles without such 5-thio substitution. Such increased absorbance coupled with the red shift of the absorbance maximum toward higher wavelengths enhances the protection of substrates sensitive to longer wavelength ultraviolet light (near visible), such as coatings, plastics and fibers.

OBJECTS OF THE INVENTION

One object of this invention is to provide 5-thio-substituted 2H-benzotriazoles having enhanced UV absorbance at longer wavelengths than the benzotriazoles of the prior art.

Another object of this invention is to provide stabilized compositions which contain an effective stabilizing amount of a 5-thio-substituted 2H-benzotriazole.

Another object of this invention is to provide 5-thio-substituted 2H-benzotriazoles which contain reactive moieties allowing them to be incorporated by chemical bonds into a variety of substrate materials thus rendering them non-migrating in respect to said substrates.

Still another object of this invention is to present a new process for the preparation of such 5-thio-substituted 2H-benzotriazoles.

DETAILED DISCLOSURE

The instant invention pertains to compounds of formula A, B or C

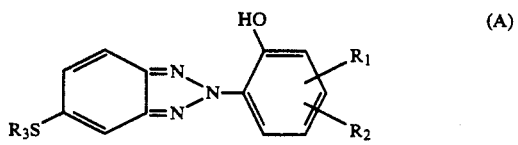

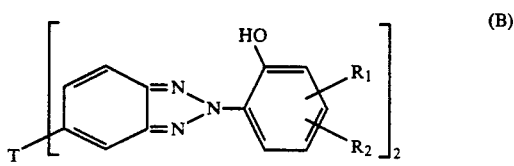

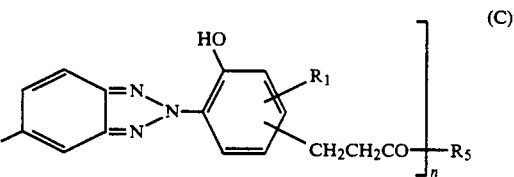

wherein $R_1$ is hydrogen, straight or branched chain alkyl of 1 to 24 carbon atoms, straight of branched chain alkenyl of 2 to 18 carbon atoms, cycloalkyl of 5 to 12 carbon atoms or phenylalkyl of 7 to 15 carbon atoms, $R_2$ is straight or branched alkyl chain of 1 to 24 carbon atoms, straight or branched chain alkenyl of 2 to 18 carbon atoms, cycloalkyl of 5 to 12 carbon atoms, phenylalkyl of 7 to 15 carbon atoms, hydroxyl, —$OR_4$ where $R_4$ is straight or branched chain alkyl of 1 to 24 carbon atoms; or said alkyl substituted by one or more —OH, —OCO—$R_{11}$, —$OR_4$, —NCO or —$NH_2$ groups or mixtures thereof; or said alkyl or said alkenyl interrupted by one or more —O—, —NH— or —$NR_4$— groups or mixtures thereof and substituted by one or more —OH, —$OR_4$ or —$NH_2$ groups or mixtures thereof; or $R_2$ is

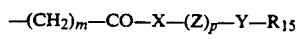

—$(CH_2)_m$—CO—X—$(Z)_p$—Y—$R_{15}$ wherein

X is —O— or —N($R_{16}$)—,

Y is —O— or —N($R_{17}$)—,

Z is $C_2$–$C_{12}$-alkylene, $C_4$–$C_{12}$-alkylene interrupted by one to three nitrogen atoms, oxygen atoms or a mixture thereof, or is $C_3$–$C_{12}$-alkylene, butenylene, butynylene, cyclohexylene or phenylene, each substituted by a hydroxyl group, m is zero, 1 or 2, p is 1, or p is also zero when X and Y are —N($R_{16}$)— and —N($R_{17}$)—, respectively, $R_{15}$ is a group —CO—C($R_{18}$)=C(H)$R_{19}$ or, when Y is —N($R_{17}$)—, forms together with $R_{17}$ a group —CO—CH=CH—CO—, wherein $R_{18}$ is hydrogen or methyl, and $R_{19}$ is hydrogen, methyl or —CO—X—$R_{20}$, wherein $R_{20}$ is hydrogen, $C_1$-$C_{12}$-alkyl or a group of the formula.

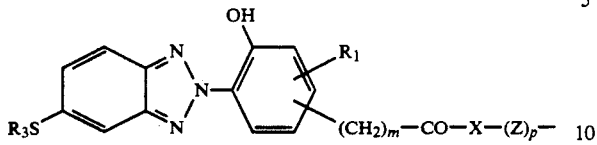

wherein the symbols $R_1$, $R_3$, X, Z, m and p have the meanings defined above, and $R_{16}$ and $R_{17}$ independently of one another are hydrogen, $C_1$-$C_{12}$-alkyl, $C_3$-$C_{12}$-alkyl interrupted by 1 to 3 oxygen atoms, or is cyclohexyl or $C_7$-$C_{15}$aralkyl, and $R_{16}$ together with $R_{17}$ in the case where Z is ethylene, also forms ethylene, n is 1 or 2, when n is 1, $R_5$ is Cl, $OR_6$ or $NR_7R_8$, or $R_5$ is —PO(OR$_{12}$)$_2$, —OSi(R$_{11}$)$_3$ or —OCO—R$_{11}$, or straight or branched chain $C_1$-$C_{24}$alkyl which is interrupted by —O—, —S— or —NR$_{11}$ and which can be unsubstituted or substituted by —OH or —OCO—R$_{11}$, $C_5$-$C_{12}$ cycloalkyl which is unsubstituted or substituted by —OH, straight chain or branched $C_2$-$C_{18}$alkenyl which is unsubstituted or substituted by —OH, $C_7$-$C_{15}$aralkyl, —CH$_2$—CHOH—R$_{13}$ or glycidyl, $R_6$ is hydrogen, straight or branched chain $C_1$-$C_{24}$alkyl which is unsubstituted or substituted by one or more OH, OR$_4$ or NH$_2$ groups, or —OR$_6$ is —(OCH$_2$CH$_2$)$_w$OH or —(OCH$_2$CH$_2$)$_w$OR$_{21}$ where w is 1 to 12 and R$_{21}$ is alkyl of 1 to 12 carbon atoms, $R_7$ and $R_8$ are independently hydrogen, alkyl of 1 to 18 carbon atoms, straight or branched chain $C_3$-$C_{18}$alkyl which is interrupted by —O—, —S— or —NR$_{11}$—, $C_5$-$C_{12}$cycloalkyl, $C_6$-$C_{14}$aryl or $C_1$-$C_3$hydroxylalkyl, or $R_7$ and $R_8$ together with the N atom are a pyrrolidine, piperidine, piperazine or morpholine ring, when n is 2, $R_5$ is one of divalent radicals —O—R$_9$—O— or —N(R$_{11}$)—R$_{10}$—N(R$_{11}$)—, $R_9$ is $C_2$-$C_8$alkylene, $C_4$-$C_8$alkenylene, $C_4$alkynylene, cyclohexylene, straight or branched chain $C_4$-$C_{10}$alkylene which is interrupted by —O— or by —CH$_2$—CHOH—CH$_2$—O—R$_{14}$—O—CH$_2$—CHOH—CH$_2$—, $R_{10}$ being straight or branched chain $C_2$-$C_{12}$alkylene which may be interrupted by —O—, cyclohexylene, or

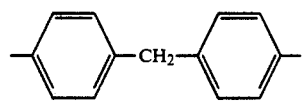

or

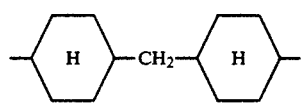

or $R_{10}$ and $R_{11}$ with the two nitrogen atoms form a piperazine ring, $R_{14}$ is straight or branched chain $C_2$-$C_8$alkylene, straight or branched chain $C_4$-$C_{10}$alkylene which is interrupted by —O—, cycloalkylene, arylene or

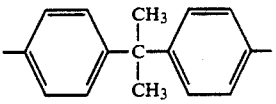

or

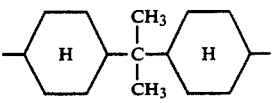

where $R_7$ and $R_8$ are independently hydrogen, alkyl of 1 to 18 carbon atoms or $R_7$ and $R_8$ together are alkylene of 4 to 6 carbon atoms, 3-oxapentamethylene, 3-iminopentamethylene or 3-methyliminopentamethylene, $R_{11}$ is hydrogen, straight or branched chain $C_1$-$C_{18}$alkyl, $C_5$-$C_{12}$cycloalkyl, straight or branched chain $C_3$-$C_8$alkenyl, $C_6$-$C_{14}$aryl or $C_7$-$C_{15}$aralkyl, $R_{12}$ is straight or branched chain $C_1$-$C_{18}$alkyl, straight or branched chain $C_3$-$C_{18}$alkenyl, $C_5$-$C_{10}$cycloalkyl, $C_6$-$C_{16}$aryl or $C_7$-$C_{15}$aralkyl, $R_{13}$ is H, straight chain or branched $C_1$-$C_{18}$alkyl which is substituted by —PO(OR$_{12}$)$_2$, phenyl which is unsubstituted or substituted by OH, $C_7$-$C_{15}$aralkyl or —CH$_2$OR$_{12}$, $R_3$ is alkyl of 1 to 20 carbon atoms, alkenyl of 3 to 18 carbon atoms, cycloalkyl of 5 to 12 carbon atoms, phenylalkyl of 7 to 15 carbon atoms, aryl of 6 to 10 carbon atoms or said aryl substituted by one or two alkyl of 1 to 4 carbon atoms or 1,1,2,2-tetrahydroperfluoroalkyl where the perfluoroalkyl moiety is of 6 to 16 carbon atoms, and T is —S—, —S—S— or —S—E—S—, where E is alkylene of 2 to 12 carbon atoms, cycloalkylene of 5 to 12 carbon atoms, or alkylene interrupted or terminated by cyclohexylene of 8 to 12 carbon atoms, and with the proviso that, when $R_1$ is sec-butyl and $R_2$ is tert-butyl, $R_3$ is not methyl.

Preferably, the instant invention pertains to compounds of formula I, II or III

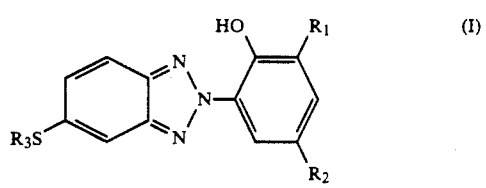

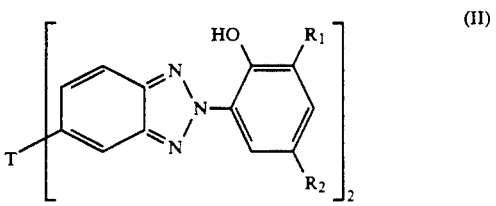

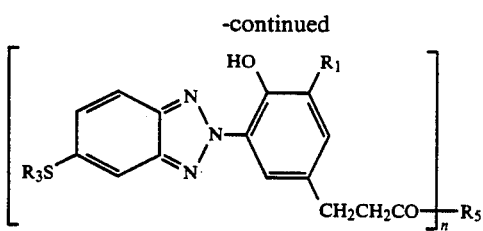

wherein

R₁ is hydrogen, straight or branched chain alkyl of 1 to 24 carbon atoms, cycloalkyl of 5 to 12 carbon atoms or phenylalkyl of 7 to 15 carbon atoms, R₂ is straight or branched chain alkyl of 1 to 24 carbon atoms, cycloalkyl of 5 to 12 carbon atoms or phenylalkyl of 7 to 15 carbon atoms; said alkyl substituted by one or more —OH, —OR₄ or —NH₂ groups where R₄ is alkyl of 1 to 12 carbon atoms; n is 1 where R₅ is —OR₆ or —NH₂; R₆ is hydrogen or alkyl of 1 to 24 carbon atoms; or said alkyl substituted by one or more —OH groups; or —OR₆ is —(OCH₂CH₂)$_w$OH or —(OCH₂CH₂)$_w$OR₂₁ where w is 1 to 12 and R₂₁ is alkyl of 1 to 12 carbon atoms, R₃ is alkyl of 1 to 20 carbon atoms, alkenyl of 3 to 18 carbon atoms, cycloalkyl of 5 to 12 carbon atoms, phenylalkyl of 7 to 15 carbon atoms, aryl of 6 to 10 carbon atoms or said aryl substituted by one or two alkyl of 1 to 4 carbon atoms, and T is —S—, —S—S— or —S—E—S—, where E is alkylene of 2 to 12 carbon atoms, cycloalkylene of 5 to 12 carbon atoms, or alkylene interrupted or terminated by cyclohexylene of 8 to 12 carbon atoms, and with the proviso that, when R₁ is sec-butyl and R₂ is tert-butyl, R₃ is not methyl.

More preferably, R₁ is hydrogen, branched alkyl of 3 to 12 carbon atoms, cyclohexyl or phenylalkyl of 7 to 9 carbon atoms, R₂ is straight or branched chain alkyl of 1 to 12 carbon atoms, cyclohexyl or phenylalkyl of 7 to 9 carbon atoms, R₃ is alkyl of 1 to 18 carbon atoms, allyl, cyclohexyl, phenylalkyl of 7 to 9 carbon atoms, phenyl or said phenyl substituted by one or two methyl groups, and T is —S— or —S—E—S, where E is alkylene of 2 to 6 carbon atoms, cycloalkylene of 6 to 8 carbon atoms or alkylene terminated by cyclohexylene of 8 to 10 carbon atoms.

Most preferably, R₁ is hydrogen, branched alkyl of 4 to 8 carbon atoms, cyclohexyl, benzyl, α-methylbenzyl or α,α-dimethylbenzyl, R₂ is straight or branched chain alkyl of 1 to 8 carbon atoms, cyclohexyl, benzyl, α-methylbenzyl or α,α-dimethylbenzyl, R₃ is phenyl, and T is —S— or —S—E—S—, where E is alkylene of 4 to 6 carbon atoms, cycloalkylene of 6 to 8 carbon atoms or dihydrolimonenediyl.

Preferred compounds are those in which one of X and Y is —O—; and particularly those in which both X and Y are —O—.

R₆, R₇ and R₈ can be the following C₃-C₁₈ alkyl radicals which are interrupted by —O—, —S—, or —NR₁₁— and can be substituted by OH: methoxyethyl, ethoxyethyl, butoxyethyl, butoxypropyl, methylthioethyl, CH₃OCH₂CH₂OCH₂CH₂—, CH₃CH₂OCH₂CH₂OCH₂CH₂—, C₄H₉OCH₂CH₂OCH₂CH₂—, ethylthiopropyl, octylthiopropyl, dodecyloxypropyl, 2-hydroxyethyl, 2-hydroxypropyl, 4-hydroxybutyl, 6-hydroxyhexyl, —CH₂CH₂—NH—C₄H₉, —CH₂CH₂CH₂NH—C₈H₁₇ and —CH₂CH₂CH₂—N(CH₃)—CH₂CH(C₂H₅)C₄H₉, R₆, R₇, R₈, R₁₁ and R₁₂ can be the following C₅-C₁₂ cycloalkyl radicals: cyclopentyl, cyclohexyl, cycloheptyl, cyclooctyl or cyclodecyl. In the case of R₆, the radical can also be substituted by —OH.

R₇, R₈ and R₁₁ can be the following alkenyl radicals: allyl, methallyl, 2-n-hexenyl or 4-n-octenyl.

When R₆ is alkenyl, it can have the same meaning as R₇, R₈ and R₁₁ as alkenyl radicals, but it can also be —CH=CH₂, n-undec-10-enyl or n-octadec-9-enyl, and it is also possible for the radical R₆ to be substituted by —OH.

R₇ and R₈ can be the following C₇-C₁₅ aralkyl radicals: benzyl, α-phenethyl, 2-phenethyl or 4-tert-butylbenzyl.

When R₁₁, R₁₃ or R₁₂ are aralkyl, they can, independently of one another, have the same meaning as R₇ or R₈.

Independently of one another, R₇, R₈ and R₁₁ can be the following C₆-C₁₄ aryl radicals: phenyl, α-naphthyl or β-naphthyl.

When R₇ and R₈ are C₁-C₃ hydroxyalkyl, they can be the following radicals: hydroxymethyl, 2-hydroxyethyl or 2-hydroxypropyl.

As C₂-C₈ alkylene, R₉ and R₁₄ can be the following radicals: ethylene, propylene, butylene, hexylene or octylene.

As alkylene, R₁₀ can be the same radicals, but can, in addition, also be higher-molecular groups such as decylene or dodecylene.

When R₉ is a C₄-C₈ alkenylene radical, the following is an example of a suitable group: butenylene.

In the case of R₉ and R₁₄, suitable straight or branched chain C₄-C₁₀ alkylene groups which are interrupted by —O— are the following groups: —CH₂CH₂OCH₂CH₂—, —CH(CH₃)—CH₂—O—CH₂—CH(CH₃)—CH₂CH₂OCH₂CH₂OCH₂CH₂— and —CH₂CH₂OCH₂CH₂OCH₂CH₂OCH₂CH₂—.

When R₁₄ is a cycloalkylene radical, the following groups are embraced: 1,3-cyclohexylene and 1,4-cyclohexylene.

When R₁₄ is arylene, this can be, specifically, the following groups: 1,3-phenylene or 1,4-phenylene.

As C₂-C₁₂-alkylene, Z is a straight or branched chain. It is for example: ethylene, propylene, tetramethylene, hexamethylene, octamethylene, dodecamethylene, 1,1-ethylidene, 2,2-propylidene, 2,2-amylidene or 2-ethylhexamethylene. C₂-C₆-alkylene groups are preferred.

When Z is C₄-C₁₂-alkylene which is interrupted by oxygen, it is for example: —CH₂—CH₂—O—CH₂—CH₂—, —CH₂—CH₂—O—CH₂—CH₂—CH₂, CH₂—CH₂—O—CH₂—CH₂—O—CH₂—CH₂ or —CH₂—CH₂—O—CH₂—CH₂—O—CH₂—CH₂—O—CH₂—CH₂—, and, when alkylene is interrupted by nitrogen, a group —N(R₁₆)— is meant, where R₁₆ is as defined in the foregoing, for example —CH₂—CH₂—NH—CH₂—CH₂—CH₂—CH₂, —CH₂—CH₂—NH—(CH₂)₈— or —CH₂CH₂—CH₂—N(CH₃—CH₂—CH(C₂H₅)(CH₂)₄—.

As C₃-C₁₂-alkylene substituted by a hydroxyl group, Z is 2-hydroxytetramethylene, 2-hydroxyhexamethylene and, in particular, 2-hydroxytrimethylene.

As cyclohexylene, Z is for example 1,4-cyclohexylene and, in particular, 1,2-cyclohexylene.

As phenylene, Z is for example m-phenylene or p-phenylene.

m can be zero, 1 or 2, but it is preferably 2.

p is preferably 1, but can also be zero if both X and Y are bound by way of introgen.

As $C_1$-$C_8$-alkyl, $R_1$ is for example: methyl, ethyl, n-propyl, isopropyl, n-butyl, sec-butyl, tert-butyl, n-pentyl, tert-amyl, n-nexyl, n-heptyl, n-octyl, 2-ethylhexyl or tert-octyl. Tert-butyl is preferred.

As $C_1$-$C_{12}$-alkyl, $R_{16}$ $R_{17}$ and $R_{20}$ can have the same meaning as that given in the foregoing for $R_1$, and can additionally be straight or branched-chain nonyl, decyl, undecyl, or dodecyl.

When $R_{16}$ and $R_{17}$ are alkyl interrupted by oxygen atoms, the examples which apply are the same as those described in the foregoing for Z.

Examples for $R_{16}$ and $R_{17}$ as aralkyl are: benzyl, α-methylbenzyl, 1-phenylethyl, α,α-dimethylbenzyl or 1-phenylpropyl.

If Z is ethylene, $R_{16}$ and $R_{17}$ together can likewise form ethylene, which is equivalent to a bridging over by way of a piperazine group.

When Y is a group —N($R_{17}$)—, $R_{15}$ and $R_{17}$ together make up a group —CO—CH=CH—CO—, and thus form the substituent

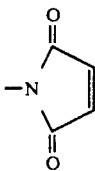

on the group —X—(Z)$_n$—.

The preferred meaning of $R_{15}$ is, however, —CO—C($R_{18}$)=CH$R_{14}$, $R_{18}$ and $R_{19}$ are preferably methyl and especially hydrogen.

$R_2$ is —CH$_2$—CH$_2$—CO—O—C(G)=CH$_2$ and G is hydrogen or methyl,

When any of $R_1$ to $R_{21}$ is alkyl, such groups are, for example, methyl, ethyl, isopropyl, n-butyl, isobutyl, sec-butyl, tert-butyl, tert-amyl, 2-ethylhexyl, tert-octyl, lauryl, tert-dodecyl, tridecyl, n-hexadecyl, n-octadecyl and eicosyl; when any of said radicals is alkenyl, such groups are, for example, allyl or oleyl; when any of said radicals is cycloalkyl, such groups are, for example, cyclopentyl, cyclohexyl, cycloheptyl, cyclooctyl and cyclododecyl; when any of said radicals are phenylalkyl, such groups are, for example, benzyl, phenethyl, α-methylbenzyl and α,α-dimethylbenzyl; and when any of said radicals is aryl, they are, for example, phenyl, naphthyl, or when substituted by alkyl are, for example, tolyl and xylyl. When $R_6$ is alkyl substituted by one or more —O— groups and/or substituted by one or more —OH, the —O$R_6$ moiety can be —(OCH$_2$CH$_2$)$_w$OH or —(OCH$_2$CH$_2$)$_w$O$R_{21}$ where w is 1 to 12 and $R_{21}$ is alkyl of 1 to 12 carbon atoms, for example.

A further preferred embodiment of the invention is a compound of formula III in which $R_1$ is tert-butyl, n is 1, $R_3$ is phenyl and $R_5$ is —O$R_6$ where $R_6$ is a straight chain or substituted octyl group. Yet another preferred embodiment of the instant invention is a compound of formula III where n is 2, $R_1$ is tert-butyl, $R_3$ is phenyl, and $R_5$ is —O—$R_9$—O— where $R_9$ is $C_2$-$C_{24}$alkylene interrupted by —O— or by —CH$_2$—CHOH—CH$_2$—O—$R_{14}$—O—CH$_2$—CHOH—CH$_2$—.

When E is alkylene, it is, for example, ethylene, tetramethylene, hexamethylene, 2-methyl-1,4-tetramethylene, hexamethylene, octamethylene, decamethylene and dodecamethylene; when E is cycloalkylene, it is, for example, cyclopentylene, cyclohexylene, cycloheptylene, cyclooctylene and cyclododecylene; and when E is alkylene interrupted or terminated by cyclohexylene, it is, for example, the saturated diyl radical derived from limonene, herein called dihydrolimonenediyl.

When the instant compounds contain a free carboxyl moiety where $R_2$ is —CH$_2$CH$_2$COO$R_6$ where $R_6$ is hydrogen, the alkali metal or amine salts of said acids are also contemplated as part of this invention allowing such UV absorbers to be used in aqueous systems due to the enhanced water solubility of such instant compounds.

The instant invention also pertains to stabilized compositions which comprise (a) an organic material subject to degradation by exposure to the deleterious effects of actinic radiation, and (b) an effective stabilizing amount of a compound of formula I, II or III.

Preferably the organic material is a synthetic polymer. Such polymers are especially those containing aromatic moieties such as polystyrene, graft copolymers of styrene such as ABS resins, polyphenylene oxides, polyphenylene sulfides, polyurethanes, polyureas, polyimides, polyamide-imides, aromatic polyesters, polycarbonates, polysulfones, polyethersulfones, polyetherketones, alkyd resins, aminoplast resins and epoxy resins.

Most preferably the synthetic polymer is an epoxy resin.

Compositions of particular interest include those which comprise (a) an organic material subject to degradation by exposure to the deleterious effects of actinic radiations which is material coated by a system consisting of a lower layer of resin which contains inorganic and/or organic pigments and an upper clear coat layer of resin, and (b) an effective stabilizing amount of a compound of formula A, B or C which is in either the upper or lower resin or in both resin layers.

The compounds of formula A, B or C of particular interest are 5-phenylthio-2-(2-hydroxy-3,5-di-tert-butylphenyl)-2H-benzotriazole, 5-phenylthio-2-[2-hydroxy-3-tert-butyl-5-(β-octyloxycarbonylethyl)phenyl]-2H-benzotriazole, 5-phenylthio-2-{2-hydroxy-3-tert-butyl-5-[2-(ω-hydroxy-octa(ethyleneoxy)-carbonylethyl]-phenyl}-2H-benzotriazole, ω-hydroxy-poly(ethyleneoxy) 3-(5-phenylthio-benzotriazol-2-yl)-5-tert-butyl-4-hydroxyhydrocinnamate, and poly(ethyleneoxy) bis[3-(5-phenylthio-benzotriazol-2-yl)-5-tert-butyl-4-hydroxyhydrocinnamate].

Other compositions of special interest include those which additionally contain a UV absorber selected from the group consisting of the benzophenones, benzotriazoles, cyanoacrylic acid derivatives, hydroxyaryl-s-triazines, organic nickel compounds and oxanilides present in either the upper or lower resin layers or in both layers.

Preferred UV absorbers are selected from the group consisting of 2-[2-hydroxy-3,5-di-(α,α-dimethylbenzyl)-phenyl]-2H-benzotriazole, 2-(2-hydroxy-3,5-di-tertamylphenyl)-2H-benzotriazole, 2-[2-hydroxy-3-tert-butyl-5-(ω-hydroxy-octa(ethyleneoxy)carbonyl)ethylphenyl]-2H-benzotriazole, 2-[2-hydroxy-3-tert-butyl-5-(2-octyloxycarbonylethyl)phenyl]-2H-benzotriazole, 4,4'-dioctyloxyoxanilide, 2,2'-dioctyloxy-5,5'-di-tert-butyloxanilide, 2,2'-didodecyloxy-5,5'-di-tert-butyloxanilide, 2-ethoxy-2'-ethyloxanilide, 2,6-bis(2,4-dimethylphenyl)-4-(2-hydroxy-4-octyloxyphenyl-s-triazine, 2,6-bis(2,4-dimethylphenyl)-4-(2,4-dihydroxyphenyl)-s-triazine, 2,4-bis(2,4-dihydroxyphenyl)-6-(4-chlorophenyl)-s-triazine, 2,6-bis(2,4-dimethylphenyl)-4-[2-hydroxy-4-(2-hydroxy-3-dodecyloxypropanoxy)phenyl]-s-triazine and 2,2'-dihydroxy-4,4'-dimethoxybenzophenone.

Additional compositions of interest include those which additionally contain an effective stabilizing amount of a phenolic antioxidant in either the upper or lower resin layers or in both layers; those which additionally contain a hindered amine derivative; or which additionally contain a phosphite or phosphonite stabilizer.

Compositions of special interest include those wherein the organic material is an enamel of high solids content used for an industrial finish; is used as a coil coating] is used as a penetrating wood finish or is used as a film-forming wood finish.

When the instant compounds also contain a reactive functional group, said compounds can be chemically bonded by either condensation or free radical addition reaction to the polymer substrate. This provides for a non-migrating, non-sublimable UV absorber stabilizer. Such reactive functional groups include hydroxy, amino, amido, carboxyl and ethylenically unsaturated moieties.

The various organic materials useful in the instant invention are described in detail later in this application as well as are the various coadditives whose concomitant use with the instant compounds is often found to be highly beneficial.

Another feature of this invention is one process by which these products are obtained, namely be reaction of 5-halosubstituted 2H-benzotriazoles with aliphatic and aromatic thiols. The reaction is preferably carried out in an aprotic polar solvent such as N,N-dimethylformamide, N,N-dimethylacetamide, N-methylpyrrolidone, dimethyl sulfoxide and the like at temperatures between 30° and 200° C. in the presence of a suitable hydrogen halide acceptor such as an alkali metal or alkaline earth metal oxide, carbonate, hydroxide and the like.

The reaction may also be carried out in non-polar hydrocarbon solvents, such as xylene or mesitylene, with the above-mentioned polar solvents as cosolvents, or in hydrocarbon solvents alone under phase-transfer conditions.

This reaction is schematically outlined in the equation given below.

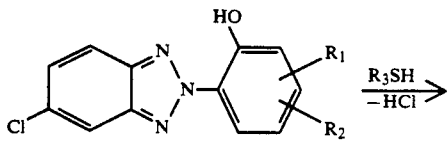

-continued

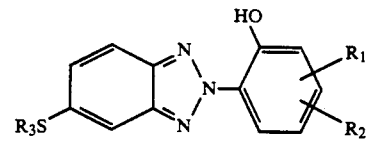

An alternative procedure for making the instant compounds involves the addition of a 5-mercaptosubstituted 2H-benzotriazole across a double bond of an unsaturated molecule. When a diene or cyclodiene is employed, a bis compound linked by the —S—E—S— moiety where E is alkylene or cycloalkylene is obtained.

As is seen in Example 12, when the procedure of using a 5-halosubstituted 2H-benzotriazole with an alkoxycarbonylsubstituted mercaptan, the expected thioether compound is not isolated. Instead a reverse Michael reaction occurs, and the product isolated is the bis-sulfide molecule where in formula B or II, T is —S—.

The bis compounds where T is —S—S— are prepared by the oxidation of the corresponding 5-mercapto substituted 2H-benzotriazoles.

In general polymers which can be stabilized include
1. Polymers of monoolefins and diolefins, for example polyethylene (which optionally can be crosslinked), polypropylene, polyisobutylene, polybutene-1, polymethylpentene-1, polyisoprene or polybutadiene, as well as polymers of cycloolefins, for instance of cyclopentene or norbornene.
2. Mixtures of the polymers mentioned under 1), for example mixtures of polypropylene with polyisobutylene.
3. Copolymers of monoolefins and diolefins with each other or with other vinyl monomers, such as, for example, ethylene/propylene, propylene/butene-1, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidene-norbornene.
4. Polystyrene, poly-(α-methylstyrene).
5. Copolymers of styrene or methylstyrene with dienes or acrylic derivatives, such as, for example, styrene/butadiene, styrene/acrylonitrile, styrene/ethyl methacrylate, styrene/butadiene/ethyl acrylate, styrene/acrylonitrile/methyl acrylate; mixtures of high impact strength from styrene copolymers and another polymer, such as, for example, from a polyacrylate, a diene polymer or an ethylene/propylene/diene terpolymer; and block polymers of styrene, such as, for example, styrene/butadiene/styrene, styrene/isoprene/styrene, styrene/ethylene/butylene/styrene or styrene/ethylene/propylene/styrene.
6. Graft copolymers of styrene, such as, for example, styrene on polybutadiene, styrene and acrylonitrile on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under 5), for instance the copolymer mixtures known as ABS-, MBS-, ASA- or AES-polymers.

7. Halogen-containing polymers, such as polychloroprene, chlorinated rubbers, chlorinated or sulfochlorinated polyethylene, epichlorohydrin homo- and copolymers, polymers from halogen-containing vinyl compounds, as for example, polyvinylchloride, polyvinylidene chloride, polyvinyl fluoride, polyvinylidene fluoride, as well as copolymers thereof, as for example, vinyl chloride/vinylidene chloride, vinyl chloride/vinyl acetate, vinylidene chloride/vinyl acetate copolymers, or vinyl fluoride/vinyl ether copolymers.

8. Polymers which are derived from $\alpha,\beta$-unsaturated acids and derivatives thereof, such as polyacrylates and polymethacrylates, polyacrylamide and polyacrylonitrile.

9. Copolymers from the monomers mentioned under 8) with each other or with other unsaturated monomers, such as, for instance, acrylonitrile/butadiene, acrylonitrile/alkyl acrylate, acrylonitrile/alkoxyalkyl acrylate or acrylonitrile/vinyl halogenide copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinylbutyral, polyallyl phthalate or polyallyl-melamine.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and those polyoxymethylenes which contain ethylene oxide as comonomer.

13. Polyphenylene oxides and sulfides, and mixtures of polyphenylene oxides with polystyrene.

14. Polyurethanes which are derived from polyethers, polyesters or polybutadienes with terminal hydroxyl groups on the one side and aliphatic or aromatic polyisocyanates on the other side, as well as precursors thereof (polyisocyanates, polyols or prepolymers).

15. Polyamides and copolyamides which are derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4-trimethylhexamethylene terephthalamide, poly-p-phenylene terephthalamide or poly-m-phenylene isophthalamide, as well as copolymers thereof with polyethers, such as for instance with polyethylene glycol, polypropylene glycol or polytetramethylene glycols.

16. Polyureas, polyimides and polyamide-imides.

17. Polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-[2,2-(4-hydroxyphenyl)-propane]terephthalate and polyhydroxybenzoates as well as block-copolyether-esters derived from polyethers having hydroxyl end groups.

18. Polycarbonates.

19. Polysulfones, polyethersulfones and polyetherketones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low flammability.

23. Thermosetting acrylic resins, derived from substituted acrylic esters, such as epoxy-acrylates, urethane-acrylates or polyester acrylates.

24. Alkyd resins, polyester resins or acrylate resins in admixture with melamine resins, urea resins, polyisocyanates or epoxide resins as crosslinking agents.

25. Crosslinked epoxide resins which are derived from polyepoxides, for example from bis-glycidyl ethers or from cycloaliphatic diepoxides.

26. Natural polymers, such as cellulose, rubber, gelatin and derivatives thereof which are chemically modified in a polymer homologous manner, such as cellulose acetates, cellulose propionates and cellulose butyrates, or the cellulose ethers, such as methyl cellulose.

27. Mixtures of polymers as mentioned above, for example PP/EPDM, Polyamide 6/EPDM or ABS, PVC/EVA, PVC/ABS, PVC/MBS, PC/ABS, PBTP/ABS.

28. Naturally occuring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, which materials may be used as plasticizers for polymers or as textile spinning oils, as well as aqueous emulsions of such materials.

29. Aqueous emulsions of natural or synthetic rubber, e.g. natural latex or latices of carboxylated styrene/butadiene copolymers.

30. Polysiloxanes such as the soft, hydrophilic polysiloxanes described, for example, in U.S. Pat. No. 4,259,467; and the hard polyorganosiloxanes described, for example, in U.S. Pat. No. 4,355,147.

31. Polyketimines in combination with unsaturated acrylic polyacetoacetate resins or with unsaturated acrylic resins. The unsaturated acrylic resins include the urethane acrylates, polyether acrylates, vinyl or acryl copolymers with pendant unsaturated groups and the acrylated melamines. The polyketimines are prepared from polyamines and ketones in the presence of an acid catalyst.

32. Radiation curable compositions containing ethylenically unsaturated monomers of oligomers and a poly-unsaturated aliphatic oligomer.

33. Epoxymelamine resins such as light-stable epoxy resins crosslinked by an epoxy functional coetherified high solids melamine resin such as LSE-4103 (Monsanto).

In general, the compounds of the present invention are employed in from about 0.01 to about 5% by weight of the stabilized composition, although this will vary with the particular substrate and application. An advantageous range is from about 0.5 to about 2%, and especially 0.1 to about 1%.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The resulting stabilized polymer compositions of the invention may optionally also contain from about 0.01 to about 5%, preferably from about 0.025 to about 2%, and especially from about 0.1 to about 1% by weight of various conventional additives, such as the materials listed below, or mixtures thereof.

1. Antioxidants 1.1. Alkylated monophenols, for example,
2,6-di-tert-butyl-4-methylphenol
2-tert.butyl-4,6-dimethylphenol
2,6-di-tert-butyl-4-ethylphenol
2,6-di-tert-butyl-4-n-butylphenol
2,6-di-tert-butyl-4-i-butylphenol
2,6-di-cyclopentyl-4-methylphenol
2-(α-methylcyclohexyl)-4,6-dimethylphenol
2,6-di-octadecyl-4-methylphenol
2,4,6-tri-cyclohexylphenol
2,6-di-tert-butyl-4-methoxymethylphenol 1.2. Alkylated hydroquinones, for example,
2,6-di-tert-butyl-4-methoxyphenol
2,5-di-tert-butyl-hydroquinone
2,5-di-tert-amyl-hydroquinone
2,6-diphenyl-4-octadecyloxyphenol 1.3. Hydroxylated thiodiphenyl ethers, for example,
2,2'-thio-bis-(6-tert-butyl-4-methylphenol)
2,2'-thio-bis-(4-octylphenol)
4,4'-thio-bis-(6-tert-butyl-3-methylphenol)
4,4'-thio-bis-(6-tert-butyl-2-methylphenol)

1.4. Alkylidene-bisphenols, for example,
2,2'-methylene-bis-(6-tert-butyl-4-methylphenol)
2,2'-methylene-bis-(6-tert-butyl-4-ethylphenol)
2,2'-methylene-bis-[4-methyl-6-(α-methylcyclohexyl)-phenol]
2,2'-methylene-bis-(4-methyl-6-cyclohexylphenol)
2,2'-methylene-bis-(6-nonyl-4-methylphenol)
2,2'-methylene-bis-[6-(α-methylbenzyl)-4-nonylphenol]
2,2'-methylene-bis-[6-(α,α-dimethylbenzyl)-4-nonylphenol]
2,2'-methylene-bis-(4,6-di-tert-butylphenol)
2,2'-ethylidene-bis-(4,6-di-tert-butylphenol)
2,2'-ethylidene-bis-(6-tert-butyl-4-isobutylphenol)
4,4'-methylene-bis-(2,6-di-tert-butylphenol)
4,4'-methylene-bis-(6-tert-butyl-2-methylphenol)
1,1-bis-(5-tert-butyl-4-hydroxy-2-methylphenyl-butane
2,6-di-(3-tert-butyl-5-methyl-2-hydroxybenzyl)-4-methylphenol
1,1,3-tris-(5-tert-butyl-4-hydroxy-2-methylphenyl)-butane
1,1-bis-(5-tert-butyl-4-hydroxy-2-methylphenyl)-3-n-dodecylmercaptobutane
ethyleneglycol bis-[3,3-bis-(3'-tert-butyl-4'-hydroxyphenyl)-butyrate]
di-(3-tert-butyl-4-hydroxy-5-methylphenyl)-dicyclopentadiene
di-[2-(3'-tert-butyl-2'-hydroxy-5'-methyl-benzyl)-6-tert-butyl-4-methylphenyl]terephthalate 1.5. Benzyl compounds, for example,
1,3,5-tri-(3,5-di-tert-butyl-4-hydroxybenzyl)-2,4,6-trimethylbenzene
di-(3,5-di-tert-butyl-4-hydroxybenzyl)sulfide
3,5-di-tert-butyl-4-hydroxybenzyl-mercapto-acetic acid isooctyl ester
bis-(4-tert-butyl-3-hydroxy-2,6-dimethylbenzyl)dithiol terephthalate
1,3,5-tris-(3,5-di-tert-butyl-4-hydroxybenzyl)isocyanurate
1,3,5-tris-(4-tert-butyl-3-hydroxy-2,6-dimethylbenzyl)isocyanurate
3,5-di-tert-butyl-4-hydroxybenzyl-phosphoric acid dioctadecyl ester
3,5-di-tert-butyl-4-hydroxybenzyl-phosphoric acid monoethyl ester, calcium-salt 1.6. Acylaminophenols, for example,
4-hydroxy-lauric acid anilide
4-hydroxy-stearic acid anilide
2,4-bis-octylmercapto-6-(3,5-tert-butyl-4-hydroxyanilino)-s-triazine
octyl-N-(3,5-di-tert-butyl-4-hydroxyphenyl)-carbamate 1.7. Esters of β-(3,5-di-tert-butyl-4-hydroxyphenyl)-propionic acid with monohydric or polyhydric alcohols, for example,

| methanol | diethylene glycol |
| octadecanol | triethylene glycol |
| 1,6-hexanediol | pentaerythritol |
| neopentyl glycol | tris-hydroxyethyl isocyanurate |
| thiodiethylene glycol | di-hydroxyethyl oxalic acid diamide |

1.8. Esters of β-(5-tert-butyl-4-hydroxy-3-methylphenyl)-propionic acid with monohydric or polyhydric alcohols, for example,

| methanol | diethylene glycol |
| octadecanol | triethylene glycol |
| 1,6-hexanediol | pentaerythritol |
| neopentyl glycol | tris-hydroxyethyl isocyanurate |
| thiodiethylene glycol | di-hydroxyethyl oxalic acid diamide |

1.9. Amides of β-(3,5-di-tert-butyl-4-hydroxyphenyl)-propionic acid for example,
N,N'-di-(3,5-di-tert-butyl-4-hydroxyphenylpropionyl)-hexamethylenediamine
N,N'-di-(3,5-di-tert-butyl-4-hydroxyphenylpropionyl)-trimethylenediamine
N,N'-di-(3,5-di-tert-butyl-4-hydroxyphenylpropionyl)-hydrazine 1.10 Diarylamines, for example, diphenylamine, N-phenyl-1-naphthylamine, N-(4-tert-octylphenyl)-1-naphthylamine, 4,4'-di-tert-octyl-diphenylamine, reaction product of N-phenylbenzylamine and 2,4,4-trimethylpentene, reaction product of diphenylamine and 2,4,4-trimethylpentene, reaction product of N-phenyl-1-naphthylamine and 2,4,4-trimethylpentene.

2. UV absorbers and light stabilizers 2.1. 2-(2'-Hydroxyphenyl)-benzotriazoles, for example, the 5'-methyl-, 3',5'-di-tert-butyl-, 5'-tert-butyl-, 5'-(1,1,3,3-tetramethylbutyl)-, 5-chloro-3',5'-di-tert-butyl-, 5-chloro-3'-tert-butyl-5'-methyl-, 3'-sec-butyl-5'-tert-butyl-, 4'-octoxy, 3',5'-di-tert-amyl-, 3',5'-bis-(α,α-dimethylbenzyl), 3'-tert-butyl-5'-(2-(omega-hydroxy-octa-(ethyleneoxy)carbonyl-ethyl)-, 3'-dodecyl-5'-methyl-, and 3'-tert-butyl-5'-(2-octyloxycarbonyl)ethyl-, and dodecylated-5'-methyl derivatives.

2.2. 2-Hydroxy-benzophenones, for example, the 4-hydroxy-, 4-methoxy-, 4-octoxy-, 4-decyloxy-, 4-dodecyloxy-, 4-benzyloxy, 4,2',4'-trihydroxy- and 2'-hydroxy-4,4'-dimethoxy derivatives.

2.3. Esters of optionally substituted benzoic acids for example, phenyl salicylate, 4-tert-butylphenyl salicylate, octylphenyl salicylate, dibenzoylresorcinol, bis-(4-tert-butylbenzoyl)-resorcinol, benzoylresorcinol, 3,5-di-tert-butyl-4-hydroxybenzoic acid 2,4-di-tert-butylphenyl ester and 3,5-di-tert-butyl-4-hydroxybenzoic acid hexadecyl ester.

2.4. Acrylates, for example, α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxy-cinnamic acid methyl ester, N-(β-carbomethoxy-β-cyanovinyl)-2-methyl-indoline.

2.5. Nickel compounds, for example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclohexyl-diethanolamine, nickel dibutyl-dithiocarbamate, nickel salts of 4-hydroxy-3,5-di-tert-butylbenzylphosphonic acid monoalkyl esters, such as of the methyl, ethyl or butyl ester, nickel complexes of ketoximes such as of 2-hydroxy-4-methyl-phenyl undecyl ketoxime, nickel complexes of 1-phenyl-4-lauroyl-5-hydroxy-pyrazole, optionally with additional ligands.

2.6. Sterically hindered amines, for example bis-(2,2,6,6-tetramethylpiperidyl) sebacate, bis-(1,2,2,6,6-pentamethylpiperidyl) sebacate, n-butyl-3,5-di-tert.butyl-4-hydroxybenzyl malonic acid bis-(1,2,2,6,6-pentanemethylpiperidyl)ester, condensation product of 1-hydroxyethyl-2,2,6,6-tetramethyl-4-hydroxypiperidine and succinic acid, condensation product of N,N'-(2,2,6,6-tetramethylpiperidyl)-hexamethylenediamine and 4-tert-octylamino-2,6-dichloro-s-triazine, tris-(2,2,6,6-tetramethylpiperidyl)-nitrilotriacetate, tetrakis-(2,2,6,6-tetramethyl-4-piperidyl) 1,2,3,4-butanetetracarboxylate, 1,1'(1,2-ethanediyl)-bis-(3,3,5,5-tetramethylpiperazinone), di-(1-octyloxy-2,2,6,6-tetramethylpiperidin-4-yl) sebacate, di-(1-cyclohexyloxy-2,2,6,6-tetramethylpiperidin-4-yl) succinate, 1-octyloxy-2,2,6,6-tetramethyl-4-hydroxy-piperidine, poly-{[6-tert-octylamino-s-triazin-2,4-diyl]}2-(1-cyclohexyloxy-2,2,6,6-tetramethylpiperidin-4-yl) imino-hexamethylene-[4-(1-cyclohexyloxy-2,2,6,6-tetramethylpiperidin-4-yl)imino], 2,4,6-tris[N-(1-cyclohexyloxy-2,2,6,6-tetramethylpiperidin-4-yl)-n-butylamino]-s-triazine.

2.7. Oxalic acid diamides, for example, 4,4'-dioctyloxy-oxanilide, 2,2'-di-octyloxy-5,5'-di-tert-butyl-oxanilide, 2,2'-di-dodecyloxy-5,5'-di-tert-butyl-oxanilide, 2-ethoxy-2'-ethyl-oxanilide, N,N'-bis(3-dimethylaminopropyl)-oxalamide, 2-ethoxy-5-tert-butyl-2'-ethyloxanilide and its mixture with 2-ethoxy-2'-ethyl-5,4'-di-tert-butyloxanilide and mixtures of ortho- and para-methoxy- as well as of o- and p-ethoxy-disubstituted oxanilides.

2.8. Hydroxyphenyl-s-triazines, for example 2,6-bis-(2,4-dimethylphenyl)-4-(2-hydroxy-4-octyloxyphenyl)-s-triazine; 2,6-bis-(2,4-dimethylphenyl)-4-(2,4-dihydroxyphenyl)-s-triazine; 2,4-bis(2,4-dihydroxyphenyl)-6-(4-chlorophenyl)-s-triazine; 2,4-bis[2-hydroxy-4-(2-hydroxyethoxy)phenyl]-6-(4-chlorophenyl)-s-triazine; 2,4-bis[2-hydroxy-4-(2-hydroxy-4-(2hydroxyethoxy)-phenyl]-6-(2,4-dimethylphenyl)-s-triazine; 2,4-bis[2-hydroxy-4-(2-hydroxyethoxy)phenyl]-6-(4-bromophenyl)-s-triazine; 2,4-bis[2-hydroxy-4-(2-acetoxyethoxy)phenyl]-6-(4-chlorophenyl)-s-triazine, 2,4-bis(2,4-dihydroxyphenyl)-6-(2,4dimethylphenyl-s-triazine.

3. Metal deactivators, for example, N,N'-diphenyloxalic acid diamide, N-salicylal-N'-salicyloylhydrazine, N,N'-bis-salicyloylhydrazine, N,N'-bis-(3,5-di-tert-butyl-4-hydroxyphenylpropionyl)hydrazine, 3-salicyloylamino-1,2,4-triazole, bis-benzylidene-oxalic acid dihydrazide.

4. Phosphites and phosphonites, for example, triphenyl phosphite, diphenylalkyl phosphites, phenyldialkyl phosphites, tri-(nonylphenyl) phosphite, trilauryl phosphite, trioctadecyl phosphite, di-stearyl-pentaerythritol diphosphite, tris-(2,4-di-tert-butylpheny) phosphite, di-isodecylpentaerythritol diphosphite, di-(2,4-di-tert-butylphenyl)pentaerythritol diphosphite, tristearyl-sorbitol triphosphite, tetrakis-(2,4-di-tert-butylphenyl) 4,4'-diphenylylenediphosphonite.

5. Compounds which destroy peroxide, for example, esters of β-thiodipropionic acid, for example the lauryl, stearyl, myristyl or tridecyl esters, mercapto-benzimidazole or the zinc salt of 2-mercaptobenzimidazole, zinc dibutyl-dithiocarbamate, dioctadecyl disulfide, pentaerythritol tetrakis-(β-dodecylmercapto)-propionate.

6. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

7. Nitrones, for example, N-benzyl-alpha-phenyl nitrone, N-ethyl-alpha-methyl nitrone, N-octyl-alpha-heptyl nitrone, N-lauryl-alpha-undecyl nitrone, N-tetradecyl-alpha-tridecyl nitrone, N-hexadecyl-alpha-pentadecyl nitrone, N-octadecyl-alpha-heptadecylnitrone, N-hexadecyl-alpha-heptadecyl nitrone, N-octadecyl-alpha-pentadecyl nitrone, N-heptadecyl-alpha-heptadecyl nitrone, N-octadecyl-alpha-hexadecyl nitrone, nitrone derived from N,N-dialkylhydroxylamine derived from hydrogenated tallow amine.

8. Polyamide stabilizers, for example copper salts in combination with iodides and/or phosphorus compounds and salts of divalent manganese.

9. Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate. 10. Nucleating agents, for example, 4-tert-butyl-benzoic acid, adipic acid, diphenylacetic acid.

11. Fillers and reinforcing agents, for example, calcium carbonate, silicates, glass fibers, asbestos, talc, kaolin, mica, barium sulfate, metal oxides and hydroxides, carbon black, graphite.

12. Other additives, for example, plasticizers, lubricants, emulsifiers, pigments, optical brighteners, flameproofing agents, anti-static agents, blowing agents and thiosynergists such as dilauryl thiodipropionate or distearyl thiodipropionate.

The phenolic antioxidant of particular interest is selected from the group consisting of n-octadecyl 3,5-di-tert-butyl-4-hydroxyhydrocinnamate, neopentanetetrayl tetrakis(3,5-di-tert-butyl-4-hydroxyhydrocinnamate), di-n-octadecyl 3,5-di-tert-butyl-4-hydroxybenzylphosphonate, 1,3,5-tris(3,5-di-tert-butyl-4-hydroxybenzyl)isocyanurate, thiodiethylene bis(3,5-di-tert-butyl-4-hydroxyhydrocinnamate), 1,3,5-trimethyl-2,4,6-tris(3,5-di-tert-butyl-4-hydroxybenzyl)benzene, 3,6-dioxaoctamethylene bis(3-methyl-5-tert-butyl-4-hydroxyhydrocinnamate), 2,6-di-tert-butyl-p-cresol, 2,2'-ethylidene-bis(4,6-di-tert-butylphenol), 1,3,5-tris(2,6-dimethyl-4-tert-butyl-3-hydroxybenzyl) isocynurate, 1,1,3,-tris(2-methyl-4-hydroxy-5-tert-butylphenyl)butane, 1,3,5-tris[2-(3,5-di-tert-butyl-4-hydroxyhydrocinnamoyloxy)ethyl]isocyanurate, 3,5-di-(3,5-di-tert-butyl-4-hydroxybenzyl)mesitol, hexamethylene bis(3,5-di-tert-butyl-4-hydroxyhydrocinnamate), 1-(3,5-di-tert-butyl-4-hydroxyanilino)-3,5-di(octylthio)-s-triazine, N,N'-hexamethylene-bis(3,5-di-tert-butyl-4-hydroxyhydrocinnamamide), calcium bis(ethyl 3,5-di-tert-butyl-4-hydroxybenzylphosphonate), ethylene bis[3,3-di(3-tert-butyl-4-hydroxyphenyl)butyrate], octyl 3,5-di-tert-butyl-4-hydroxybenzylmercaptoacetate, bis(3,5-di-tert-butyl-4-hydroxyhydrocinnamoyl)hydrazide, and N,N'-bis[2-(3,5-di-tert-butyl-4-hydroxyhydrocinnamoyloxy)-ethyl]-oxamide.

A most preferred phenolic antioxidant is neopentanetetrayl tetrakis(3,5-di-tert-butyl-4-hydroxyhydrocinnamate), n-octadecyl 3,5-di-tert-butyl-4-hydroxyhydrocinnamate, 1,3,5-trimethyl-2,4,6-tris(3,5-di-tert-butyl-4-hydroxybenzyl)benzene, 1,3,5-tris(3,5-di-tert-butyl-4-hydroxybenzyl)isocyanurate, 2,6-di-tert-butyl-p-cresol or 2,2'-ethylidene-bis(4,6-di-tert-butylphenol).

The hindered amine compound of particular interest is selected from the group consisting of bis(2,2,6,6-tetramethylpiperidin-4-yl) sebacate, bis(1,2,2,6,6-pentamethylpiperidin-4-yl) sebacate, di(1,2,2,6,6-pentamethylpiperidin-4-yl) (3,5-di-tert-butyl-4-hydroxybenzyl)-butylmalonate, 4-benzoyl-2,2,6,6-tetramethylpiperidine, 4-stearyloxy-2,2,6,6-tetramethylpiperidine, 3-n-octyl-7,7,9,9-tetramethyl-1,3,8-triaza-spiro[4.5]decane-2,4-dione, tris(2,2,6,6-tetramethylpiperidin-4yl) nitrilotriacetate, 1,2-bis(2,2,6,6-tetramethyl-3-oxopiperazin-4-yl)ethane, 2,2,4,4-tetramethyl-7-oxa-3,20-diaza-21-oxodispiro[5.1.11.2]heneicosane, polycondensation product of 2,4-dichloro-6-tert-octylamino-s-triasine and 4,4'-hexamethylenebis(amino-2,2,6,6-tetramethylpiperidine), polycondensation product of 1-(2-hydroxyethyl)-2,2,6,6-tetramethyl-4-hydroxypiperidine and succinic acid, polycondensation product of 4,4'-hexamethylenebis-(amino-2,2,6,6-tetramethylpiperidine) and 1,2-dibromoethane, tetrakis(2,2,6,6-tetramethylpiperidin-4-yl) 1,2,3,4-butanetetracarboxylate, tetrakis(1,2,2,6,6-pentamethylpiperidin-4-yl) 1,2,3,4-butanetetracarboxylate, polycondensation product of 2,4-dichloro-6-morpholino-s-triazine and 4,4'-hexamethylenebis(amino-2,2,6,6-tetramethylpiperidine), N,N',N'',N'''-tetrakis[(4,6-bis(butyl-2,2,6,6-tetramethyl-piperidin-4-yl)-amino-s-triazin-2-yl]-1,10-diamino-4,7-diazadecane, mixed[2,2,6,6-tetramethylpiperidin-4-yl/$\beta,\beta,\beta',\beta'$-tetramethyl-3,9-(2,4,8,10-tetraoxaspiro[5.5]-undecane) diethyl]1,2,3,4-butanetetracarboxylate, mixed[1,2,2,6,6-pentamethylpiperidin-4-yl/$\beta,\beta,\beta',\beta'$-tetramethyl-3,9-(2,4,8,10-tetraoxaspiro[5.5]-undecane) diethyl]1,2,3,4-butanetetracarboxylate, octamethylene bis(2,2,6,6-tetramethylpiperidin-4-carboxylate), 4,4'-ethylenebis(2,2,6,6-tetramethylpiperazin-3-one), N-2,2,6,6-tetramethylpiperidin-4-yl-n-dodecylsuccinimide, N-1,2,2,6,6-pentamethylpiperidin-4-yl-n-dodecylsuccinimide, N-1-acetyl-2,2,6,6-tetramethylpiperidin-4-ylndodecylsuccinimide, 1-acetyl3-dodecyl-7,7,9,9-tetramethyl-1,3,8-triazaspiro[4.5]decane-2,4-dione, di-(1-octyloxy-2,2,6,6-tetramethylpiperidin-4-yl) sebacate, di-(1-cyclohexyloxy-2,2,6,6-tetramethylpiperidin-4-yl) succinate, 1-octyloxy-2,2,6,6-tetramethyl-4-hydroxy-piperidine, poly-{[6-tert-octylamino-s-triazin-2,4-diyl]}2-(1-cyclohexyloxy-2,2,6,6-tetramethylpiperidin-4-yl)imino-hexamethylene-[4-(1-cyclohexyloxy-2,2,6,6-tetramethylpiperidin-4-yl)imino], and 2,4,6-tris[N-(1-cyclohexyloxy-2,2,6,6-tetramethylpiperidin -4-yl)-n-butylamino]-s-triazine.

A most preferred hindered amine compound is bis(2,2,6,6-tetramethylpiperidin-4-yl) sebacate, bis(1,2,2,6,6-pentamethylpiperidin-4-yl) sebacate, di(1,2,2,6,6-pentamethylpiperidin-4-yl) (3,5-di-tert-butyl-4-hydroxybenzyl)butylmalonate, the polycondensation product of 1-(2-hydroxyethyl)-2,2,6,6-tetramethyl-4-hydroxypiperidine and succinic acid, the polycondensation product of 2,4-dichloro-6-tert-octylamino-s-triazine and 4,4'-hexamethylenebis(amino-2,2,6,6-tetramethylpiperidine), N,N',N'',N'''-tetrakis[(4,6-bis(butyl-(2,2,6,6-tetramethyl-piperidin-4-yl)amino)-s-triazine-2-yl]-1,10-diamino-4,7-diazadecane, di-(1-octyloxy-2,2,6,6-tetramethylpiperidin-4-yl) sebacate, di-(1-cyclohexyloxy-2,2,6,6-tetramethylpiperidin-4-yl) succinate, 1-octyloxy-2,2,6,6-tetramethyl-4-hydroxypiperidine, poly-{[6-tert-octylamino-s-triazin-2,4-diyl]}2-(1-cyclohexyloxy-2,2,6,6-tetramethylpiperidin-4-yl)imino-hexamethylene-[4-(1-cyclohexyloxy-2,2,6,6-tetramethylpiperidin-4-yl)imino], or 2,4,6-tris[N-(1-cyclohexyloxy-2,2,6,6-tetramethylpiperidin-4-yl)-n-butylamino]-s-triazine.

The following examples are presented for the purpose of illustration only and are not to be construed to limit the nature or scope of the instant invention in any manner whatsoever.

EXAMPLE 1

5-n-Dodecylthio-2-(2-hydroxy-3,5-di-tert-butylphenyl)-2H-benzotriazole

To a 3-liter three-necked flask equipped with stirrer, thermometer, nitrogen inlet and distillation set-up are charged 357.8 g (1 mole) of 5-chloro-(2-hydroxy-3,5-di-tert-butylphenyl)-2H-benzotriazole, available from CIBA-GEIGY Corp. as TINUVIN ® 327,216.8 g (1.05 mole) of n-dodecyl mercaptan and 600 mL of N,N-dimethylformamide (DMF). Then 73.9 g (0.54 moles) of potassium carbonate and 2 g of potassium iodide are added and the mixture heated for 20 hours at 150° C. under a nitrogen atmosphere. Any water which is liberated as a result of the reaction distills off as an azeotrope until the head-temperature reaches 132° C. After 20 hours at 150° C. the starting 2H-benzotriazole is totally consumed. With partial vacuum at 80°-100° C., most of the DMF is distilled off. To the resulting oil is added at 80° C. 1L of toluene and 500 mL of water. The aqueous phase is drained off. The toluene solution is washed twice more with 500 mL water containing 1 mL of acetic acid. The organic solution is freed from residual water by azeotropic distillation until a clear solution is obtained. Under partial vacuum all but about 100 mL of toluene is distilled off at 70° C. The residue is diluted at 60° C. with 2 L of isopropanol and some product seeds are added. The product gradually crystallizes and the mixture is slowly cooled to 10° C. The product is filtered off and washed with 300 mL of isopropanol to yield 490.4 g (93.6% of theory) of the title compound, mp. 62°-64° C.

EXAMPLE 2

5-Phenylthio-2-(2-hydroxy-3,5-di-tert-butylphenyl)-2H-benzotriazole

Into a two-liter three-necked flask equipped with stirrer, thermometer, distillation set-up and nitrogen supply are charged 268.4 g (0.75 mole) of 5-chloro-2-(2- hydroxy-3,5-di-tert-butylphenyl)-2H-benzotriazole, 93.7 g (0.825 mole) of thiophenol and 400 mL of N,N-dimethylformamide (DMF). The reactor is evacuated and filled with nitrogen three times to establish an inert atmosphere. To the slurry is added 66.0 g (0.825 mole) of 50% aqueous sodium hydroxide solution and the mixture heated to reflux. At this point water distills off as an azeotrope until the head-temperature reaches 132° C. and a reaction temperature of 150° C. After 18 hours there is no residual starting benzotriazole compound observed (TLC). At reduced pressure most of the DMF is distilled off at 80° C. To the residue is then charged 500 mL of toluene and 200 mL of water. After slow stirring for a few minutes at 80° C. the lower aqueous phase is drained off. The addition of 200 mL of water is repeated twice more, the second time with addition of 1 mL of acetic acid. Any residual water is azeotroped off until a clear solution is obtained. Approximately 300 mL of toluene is removed under partial vacuum at 90° C. and to the concentrate is added 800 mL of isopropanol, resulting in rapid crystallization. The reaction mixture is cooled to 20° C. and filtered. The light yellow crystals are washed with 250 ml of isopropanol and dried to give 317 g (97.9% of theory) of the title compound, mp. 132°–134° C.

Alternatively, the title compound is also synthesized as seen below:

To a 250 ml round-bottomed flask equipped with a magnetic stirrer, a nitrogen inlet and condenser are charged 3.0 g (0.0084 mol) of 5-chloro-2-(2-hydroxy-3,5-di-tert-butylphenyl2H-benzotriazole, 1.1 g (0.020 mol) of ground potassium hydroxide, 1.6 ml (0.016 mol) of thiophenol, 0.135 g (0.49 mol) 18-crown-6, and 9 ml of mesitylene. The mixture is refluxed with stirring for four hours and then allowed to cool to room temperature. Ethyl acetate and 2N hydrochloric acid are added. The layers are separated and the organic layer is washed once with water and once with brine, and finally dried over anhydrous magnesium sulfate. Analysis of the crude mixture by nmr (CDCl$_3$) shows that conversion to the desired title compound product is about 15%.

EXAMPLES 3-13

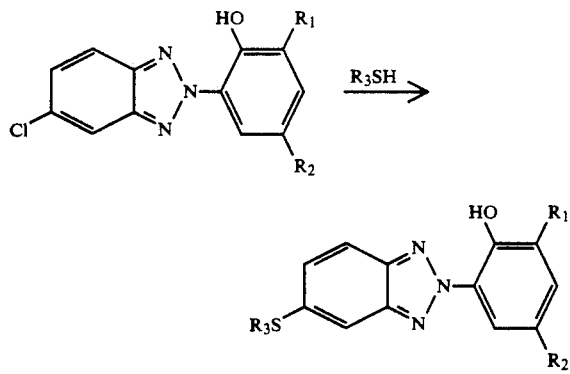

Using the general methods of Examples 1 and 2, the following compounds are obtained analogously, typically with yields exceeding 90%.

| Example | R$_1$ | R$_2$ | R$_3$* | M.P. (°C.) |
|---|---|---|---|---|
| 3 | H | methyl | phenyl | 109–111 |

-continued

| Example | R$_1$ | R$_2$ | R$_3$* | M.P. (°C.) |
|---|---|---|---|---|
| 4 | t-butyl | methyl | benzyl | 139–141 |
| 5 | t-butyl | methyl | phenyl | 131–133 |
| 6 | t-butyl | t-butyl | n-octyl | 79–81 |
| 7 | t-butyl | t-butyl | tridecyl | resinous |
| 8 | t-butyl | t-butyl | hexamethylene(bis) | 127–130 |
| 9 | t-butyl | t-butyl | limonenediyl (bis) | resinous |
| 10 | t-octyl | t-octyl | phenyl | 84–86 |
| 11 | α-cumyl | α-cumyl | phenyl | 118–120 |
| 12 | t-butyl | CH$_2$CH$_2$COOH (β-carboxyethyl) | phenyl | 156–157 |
| 13 | t-butyl | CH$_2$CH$_2$COOR$_6$ R$_6$ is octyl | phenyl | oil |

*for Examples 8 and 9, this is E in formula II

EXAMPLE 13

5-Phenylthio-2-[2-hydroxy-3-tert-butyl-5-(β-octyloxycarbonylethyl)phenyl]-2H-benzotriazole To a 1 liter, 3-necked round-bottomed flask equipped with a magnetic stirrer, nitrogen inlet, serum stopper, and a condenser are charged 40.77 g (0.084 mol) of 5-chloro-[2-hydroxy3-tert-butyl-5-(β-octyloxycarbonylethyl)phenyl]-2H-benzotriazole, available from CIBA-GEIGY Corp. as TINUVIN® 109, 5.8 g (0.042 mol) of potassium carbonate, and 1 g potassium iodide. The mixture is placed under a nitrogen atmosphere, and 210 mL of N,N-dimethylformamide are quickly added. The solution is heated to 130°–140° C., and 10.1 g (0.092 mol) of thiophenol are added all at once via a syringe. The reaction mixture is stirred at this temperature for 21 hours, and is then allowed to cool to room temperature. The mixture is neutralized with a small portion of acetic acid, ethyl acetate and brine are added, and the layers are separated. The aqueous layer is extracted twice with ethyl acetate, and the combined organic layers are washed twice with brine and twice with water, and finally are dried over anhydrous magnesium sulfate. The mixture is filtered and passed through a plug of silica gel. The solvent is stripped to afford 53.8 g of a yellow oil. The oil is purified by medium pressure chromatography on a silica gel column to yield 29.7 g (63%) of the title compound as a clear yellow oil.

Analysis: Calcd. for C$_{33}$H$_{41}$N$_3$O$_3$S: C, 70.8; H, 7.4; N, 7.5. Found: C, 70.6; H, 7.8; N, 7.9.

Likewise, to a 250 mL round-bottomed flask equipped with a magnetic stirrer, nitrogen inlet, condenser, and a Dean-Stark trap are charged 4.3 g (0.0096 mol) of 3-(5-phenylthio-2H-benzotriazol-2-yl)-5-tert-butyl-4-hydroxyhydrocinnamic acid, 3.4 g (0.026 mol) of Exxel 8, an isomeric mixture of octanols available from Exxon Chemicals, 70 mg of p-toluenesulfonic acid, and 20 mL of xylene. The mixture is refluxed 3.5 hours, is cooled to room temperature, and a portion of ethyl acetate is added. The solution is washed once with water, twice with saturated sodium bicarbonate solution, and once with brine. After drying over anhydrous magnesium sulfate, the solvent is removed under reduced pressure to afford 5.17 g (96% yield) of the title compound as a viscous yellow oil. Analysis by nmr (CDCl$_3$) is consistent with the structure of the title compound.

EXAMPLE 14

5,5'-Thiobis-[2-(2-hydroxy-3,5-di-tert-butylphenyl)-2H-benzotriazole]

6.4 g (0.06 Mole) of 3-mercaptopropionic acid is dissolved in a solution of 2.76 g of sodium and 80 mL of ethanol. The solvent is stripped off and replaced with 110 mL of N,N-dimethylacetamide and 17.9 g (0.05 mole) of 5-chloro-2-(2-hydroxy-3,5-di-tert-butylphenyl)-2H-benzotriazole is added. The mixture is heated under a nitrogen atmosphere at 160°-165° C. for 48 hrs. TLC showed the presence of some unreacted benzotriazole starting material. The cooled mixture is poured into water containing 150 mL of toluene and neutralized with hydrochloric acid. The toluene solution is separated and washed with water, dried over anhydrous magnesium sulfate and filtered. The solution is concentrated and diluted with ethanol. The resulting solid is isolated by filtration and washed with acetone to extract unreacted starting material. The filter cake is dissolved in 25 mL of toluene at 70° C. and 35 mL of acetone is added to precipitate the product. The resulting crystals are filtered off and washed with acetone to give 6.6 g. of the title compound, mp. 245°-246° C.

The same product is obtained when mercaptoacetic acid is used in place of 3-mercaptopropionic acid.

EXAMPLE 15

5-Phenylthio-2-[2-hydroxy-3-tert-butyl-5-(3-hydroxypropyl)phenyl]-2H-benzotriazole To a suspension of lithium aluminum hydride (6.0 g, 0.16 mol) in 500 mL anhydrous diethyl ether in a 2 liter Erlenmeyer flask with magnetic stirring is added dropwise at room temperature a solution of 30.1 g (0.078 mol) of 5-chloro-2-[2-hydroxy-3-tert-butyl-5-(2-methoxycarbonylethyl)phenyl]-2H-benzotriazole in 500 ml of anhydrous diethyl ether. The mixture is stirred for an additional 1.5 hour at room temperature, and excess hydride is quenched with ethyl acetate. Water is added until a gel is formed; the mixture is dried over anhydrous magnesium sulfate, filtered, and the solvent is removed in vacuo to afford 28.7 g (100% yield) of the intermediate compound as a yellow-orange solid; mp 105°-106° C.

To a 1 liter round-bottomed flask equipped with magnetic stirring, a condenser, and a nitrogen atmosphere is charged 27.7 g (0.077 mol) of the intermediate compound prepared above, 10.6 g (0.077 mol) of potassium carbonate, 1.2 g of potassium iodide, and 8.48 g (0.077 mol) of thiophenol in 240 ml of N,N-dimethylformamide. A preheated oil bath is applied (165° C.), and the mixture is stirred at this temperature for 4.5 hours. After cooling to room temperature, stirring is continued for an additional 18 hours. The reaction mixture is then poured into 500 mL water. The aqueous layer is neutralized with concentrated hydrochloric acid, and is then extracted three times with ethyl acetate. The combined organic layers are washed twice with 1N hydrochloric acid, once with brine, and then dried over anhydrous magnesium sulfate. The solvent is removed under reduced pressure to afford 30.1 g of a yellow-orange solid. The crude material is recrystallized from heptane to afford 26.3 g (79% yield) of the title compound as yellow powder.

Analysis: Calcd for $C_{25}H_{27}N_3O_2S$: C, 69.3; H, 6.3; N, 9.7. Found: C, 68.9; H, 6.0; N, 9.7.

EXAMPLE 16

3-(5-Phenylthio-2H-benzotriazol-2-yl)-5-tert-butyl-4-hydroxyhydrocinnamic acid To a 1 liter, 4 necked, round-bottomed flask equipped with mechanical stirring and a nitrogen atmosphere is charged 100.0 g (0.258 mol) of methyl 3-(5-chloro-2H-benzotriazol-2-yl)-5-tert-butyl-4-hydroxyhydrocinnamate, 350 mL of N,N-dimethylformamide, and 61.9 g (0.773 mol) of 50% aqueous sodium hydroxide solution. The mixture is heated at 75°-80° C. for 3 hours at which point the ester hydrolysis is complete. A catalytic amount of potassium iodide (5.0 g) is added. Thiophenol (32.2 g, 0.258 mol) is then added over a 20 minute period while the temperature remains at 75°-80° C. An additional portion of N,N-dimethylformamide (200 mL) is added during the addition of thiophenol to facilitate stirring. A 25 mL fraction of water/methanol is removed and the solution is refluxed for 48 hours. The reaction mixture is cooled, then partitioned between 1.0 L of 1N hydrochloric acid and 1.0 L of ethyl acetate. The phases are separated and the organic phase is dried over anhydrous magnesium sulfate, and the solvent is then removed under reduced pressure until the total volume is 500 mL. To this is added 200 mL of heptane and the solution is allowed to sit overnight. The resultant crystals are collected by vacuum filtration, washed with 9:1 heptane:ethyl acetate, and dried to afford 83.5 g (72% yield) of the title compound; mp 154°-156° C.

EXAMPLE 17

3-(5-Phenylthio-2H-benzotriazol-2yl)-5-tert-butyl-4-hydroxyhydrocinnamamide

To a dry, 500 mL round-bottomed flask equipped with magnetic stirring, a condenser, and a nitrogen inlet is charged 3.0 g (0.0067 mol) of 3-(5-phenylthio-2H-benzotriazol-2-yl)-5-tert-butyl-4-hydroxyhydrocinnamic acid, 6 mL of oxalyl chloride, and enough chloroform to form a homogeneous solution (ca. 4 mL). The solution is refluxed for 1 hour and then stirred overnight at room temperature. The oxalyl chloride is distilled off under reduced pressure to afford ca. 3.5 g of a yellow solid. An IR spectrum of the solid (thin film from chloroform) reveals complete formation of the acid chloride (1795 $cm^{-1}$) intermediate.

To a 500 mL round-bottomed flask equipped with magnetic stirring is charged 250 mL of anhydrous ethanol. After cooling to $-5°$ C., ammonia gas is bubbled through the solvent until ca. 1 g (0.06 mol) is taken up. The acid chloride is added to the ammonia solution quickly in small portions, producing a red solution. The mixture is allowed to warm to room temperature, and is stirred overnight. The ethanol is removed under reduced pressure, and the residue is taken up in ethyl acetate. The solution is washed with water (1×), saturated sodium carbonate (1×), and brine (1×). The combined aqueous layers are extracted twice with ethyl acetate and the combined organic layers are dried over anhydrous magnesium sulfate. Removal of the solvent affords 3.1 g of a brown solid. The crude product is recrystallized from ethanol/water to afford 1.85 g (62% yield) of the pure amide as a brown solid; mp 128°-130° C.

Analysis: Calcd. for $C_{25}H_{26}N_4O_2S$: C, 67.2; H, 5.9; N, 12.5. Found: C, 66.7; H, 5.7; N, 12.3.

EXAMPLE 18

An isomeric mixture of
3-[3-(5-Phenylthio-2H-benzotriazol-2-yl)-5-tert-butyl-4-hydroxyhydrocinnamoyloxy]-2-hydroxypropyl Methacrylate and
2-[3-(5-Phenylthio-2H-benzotriazol-2-yl)-5-tert-butyl-4-hydroxyhydrocinnamoyloxy]-3-hydroxypropyl Methacrylate To a 250 mL round-bottomed flask equipped with magnetic stirring is charged 20.0 g (0.0447 mol) of 3-(5-phenylthio-2H-benzotriazol-2-yl)-5-tert-butyl-4-hydroxyhydrocinnamic acid, 0.20 g of 4-methoxyphenol, 1.50 g of tetrabutylammonium bromide, 6.60 g (0.0460 mol) of glycidyl methacrylate, and 150 mL of toluene. The stirred mixture is refluxed for 6 hours. After allowing to cool to room temperature the mixture is washed with water (1×) and the solvent is removed in vacuo to afford 27.3 g (100% yield) of the title compounds as a pale yellow viscous oil. Analysis by nmr reveals that the product is an isomeric mixture of A and B (A:B, 78:22).

Analysis: Calcd. for $C_{32}H_{35}N_3O_6S$: C, 65.2; H, 6.0; N, 7.1. Found: C, 66.9; H, 6.6; N, 6.5.

EXAMPLE 19

5-Phenylthio-2-{2-hydroxy-3-tert-butyl-5-[2-(ω-hydroxy-octa(ethyleneoxy)-carbonylethyl]phenyl}-2H-benzotriazole and
3,6,9,12,15,18,21-Heptaoxatricosylmethylene Bis-[3-(5-phenylthio2H-benzotriazol-2-yl)-5-tert-butyl-4-hydroxyhydrocinnamate]

To a 250 ml round-bottomed flask equipped with a magnetic stirrer, nitrogen inlet, condenser and a Dean-Stark trap are charged 4,43 g (0.01 mol) of 3-(5-phenylthio-2H-benzotriazol-2-yl)-5-tert-butyl-4-hydroxyhydrocinnamic acid, 8.0 g (0.027 mol) of polyethylene glycol of formula $H(OCH_2CH_2)_wOH$ (available from Shell Chemical Co. as PEG 300 with an average molecular weight of 300 where w is 4-11 and is on average about 7 or 8), 70 mg of p-toluenesulfonic acid, and 20 ml of xylene. The mixture is refluxed for 23 hours and is then allowed to cool to room temperature. Ethyl acetate is added and the solution is washed thrice with saturated sodium carbonate solution and once with brine. The organic layer is separated and dried over anhydrous magnesium sulfate. The solvent is removed under reduced pressure to afford a 50/50 mixture of the title compounds in a yield of 6.36 g (100%) as a viscous yellow oil. Analysis by nmr ($CDCl_3$) is consistent with the desired title compounds.

EXAMPLE 20

Spectral Properties of Substituted 5-Thiobenzotriazole UV-Absorbers

The following table shows the absorption maxima, molar and specific extinction coefficients of a number of 2H-benzotriazole UV-absorbers. A state-of-the-art commercial benzotriazole UV-absorber, 2-[2-hydroxy-3,5-di-(α,α-dimethylbenzyl)phenyl]-2H-benzotriazole, and a number of instant 5-thiosubstituted compounds are tested. The concentrations of each of the samples are identical, namely 20 mg/L. The absorption maxima of the thio compounds at 363 to 369 nm are red-shifted, i.e. shifted towards the visible by at least 20 nm relative to the commercial control, which has an absorption maximum at 342 nm (ε 15,500). The molar extinction coefficients of the thio substituted instant compounds far exceed that of the control compound at the absorption maxima.

| Absorption Maxima and Molar Extinction Coefficients of Benzotriazole UV Absorbers | | | | |
|---|---|---|---|---|
| Compound of | nm | Molar ε | nm | Molar ε |
| Control* | 302 | (15,200) | 342 | (15,500) |
| Example 1 | 307 | (8,700) | 365 | (23,300) |
| Example 2 | 310 | (8,400) | 365 | (22,300) |
| Example 3 | 294 | (8,900) | 363 | (23,700) |
| Example 4 | 311 | (8,900) | 365 | (22,900) |
| Example 5 | 309 | (9,200) | 366 | (22,800) |
| Example 6 | 310 | (8,900) | 366 | (22,400) |
| Example 8 | 310 | (16,800) | 365 | (43,200) |
| Example 9 | 318 | (16,700) | 363 | (15,700) |
| Example 10 | 312 | (10,000) | 367 | (22,900) |
| Example 11 | 309 | (9,700) | 366 | (24,000) |
| Example 14 | 310 | (19,800) | 369 | (41,700) |

*Control is 2-[2-hydroxy-3,5-di-(α,α-dimethylbenzyl)phenyl]-2H-benzotriazole.

EXAMPLE 21

The novel UV absorbers of this invention are particularly effective for the protection of substrates that are sensitive to relatively long wavelength UV light. This includes many aromatic systems. Epoxy resins which are important primers in automotive and other industrial application are an important example. Light can penetrate automotive clear and basecoats and destroy the primer at the primer/basecoat interface. This is then accompanied by loss of topcoat adhesion, even though the topcoat itself may still be in excellent condition. Exposure to high humidity facilitates this delamination phenomenon.

Steel test panels containing a commercial epoxy primer, deposited by cathodic electrodeposition, are prepared by spray applying a 1.8-2.0 mil (0.046-0.051 mm) thick film of a commercially available high solids thermoset acrylic melamine clearcoat directly over the 4"×12" (10.16 cm×30.48 cm) UNIPRIME panels obtained from Advance Coating Technology, Inc. The coated panels are then baked at 250° F. (121° C.) for 30 minutes. After storage for 1 week in an air-conditioned room, the coated panels are exposed for 55 days in Florida at 5 degrees south black box according to SAE J1976. The panels receive 56 MJ/m² of UV radiation. The unstabilized control panel delaminates during the outdoor exposure and is not subjected to further testing. The remaining panels are then placed in a QCT humidity cabinet (Q-Panel Co.) at 100% relative humidity and checked daily for blistering and delamination. The results are shown in the following table.

| Humidity Resistance of High Solids Thermoset Acrylic Clearcoats Applied over Electrocoat Primer After 55 Days Florida Exposure | | | | |
|---|---|---|---|---|
| 3% by weight of Compound of Example | Day 1 | Day 2 | Day 3 | Day 4 |
| unstabilized | delaminated during exposure in Florida | | | |
| UVA 1* | 8, dense | delaminated | — | — |
| UVA 2* | 8, dense | delaminated | — | — |
| UVA 3* | delaminated | — | — | — |
| Example 1 | none | none | none | none |
| Example 2 | none | none | none | none |
| Example 3 | none | none | none | none |
| Example 6 | none | none | none | none |

-continued

| Humidity Resistance of High Solids Thermoset Acrylic Clearcoats Applied over Electrocoat Primer After 55 Days Florida Exposure | | | | |
|---|---|---|---|---|
| 3% by weight of Compound of Example | Day 1 | Day 2 | Day 3 | Day 4 |
| Example 11 | none | none | none | none |

*UVA 1 is 2-(2-hydroxy-3,5-di-tert-amylphenyl)-2H-benzotriazole.
UVA 2 is 2-[2-hydroxy-3,5-di(α,α-dimethylbenzyl)phenyl]-2H-benzotriazole.
UVA 3 is 2-[2-hydroxy-3-tert-butyl-5-(2-ω-hydroxy-octa(ethyleneoxy)-carbonyl)ethylphenyl]-2H-benzotriazole.

After the fourth day of humidity exposure, the panels containing clearcoats stabilized by 3% by weight of an instant compound of Example 1, 2, 3, 6, or 11 are tested for adhesion according to ASTM D-3359. All panels are rated at 3-4B where 5B indicates no loss of adhesion and 0B indicates greater than 65% loss of adhesion.

These results indicate that the instant 2H-benzotriazoles having enhanced adsorption in the near visible range are particularly effective in protecting automotive coatings from delamination after prolonged exposure to sunlight and high humidity conditions.

EXAMPLE 22

Delamination Resistance of High Solids Thermoset Clearcoats Containing UV-Absorbers Applied Directly over Electrocoat Primer Steel test panels containing a commercial epoxy primer, deposited by cathodic electrodeposition, are prepared by spray applying a 1.8-2.0 mil (0.036-0.051 mm) thick film of a commerically available high solids thermoset acrylic melanmine clearcoat containing the indicated amount of the test UV-absorber directly over the 4"×12" (10.16 cm×30.48 cm) UNIPRIME ® panels obtained from Advance Coating Technology, Inc. The coated panels are then baked at 250° F. (121° C.) for 30 minutes. After storage for one week in an air-conditioned room, the panels are exposed in Florida at 5 degrees South in a black box according to SAE J-1976. The panels are evaluated every 7 days for delamination and are deemed to have failed when delamination is evident on at least 10 percent of the panel. The results of this Florida exposure are seen in the table below.

| UV-Absorber of | Wt % UV-Absorber | Days till Delamination |
|---|---|---|
| none | — | 7 |
| UVA-4* | 1.0 | 38 |
| UVA-4* | 3.0 | 56 |
| Example 13 | 1.0 | 34 |
| Example 13 | 3.0 | 97 |

*UVA is 2-{2-hydroxy-3-tert-butyl-5-[2-(octyloxycarbonyl)ethyl]phenyl}-2H-benzotriazole.

EXAMPLE 23

Delamination Resistance of High Solids Thermoset Clearcoats Containing UV-Absorbers Applied Directly over Electrocoat Primer Steel test panels containing a commercial epoxy primer, deposited by cathodic electrodeposition, are prepared by spray applying a 1.8-2.0 mil (0.036-0.051 mm) thick film of a commerically available high solids thermoset acrylic melamine clearcoat containing the indicated amount of the test UV-absorber directly over the 4"×12" (10.16 cm×30.48 cm) UNIPRIME ® panels obtained from Advance Coating Technology, Inc. The coated panels are then baked at 250° F. (121° C.) for 30 minutes. After storage for one week in an air-conditioned room, the panels are exposed in Florida at 5 degrees South in a black box according to SAE J-1976. The panels are evaluated every 7 days for delamination and are deemed to have failed when delamination is evident on at least 10 percent of the panel. The results of this Florida exposure are seen in the table below.

| UV-Absorber of | Wt % UV-Absorber | Days till Delamination |
|---|---|---|
| none | — | 19 |
| UVA-4* | 2.0 | 101 |
| Example 2 | 2.0 | >228 |

*UVA-4 is 2-{2-hydroxy-3-tert-butyl-5-[2-(octyloxycarbonyl)ethyl]phenyl}-2H-benzotriazole.

EXAMPLE 24

Copolymer of an isomeric mixture of
3-[3-(5-Phenylthio-2H-benzotriazol-2-yl)-5-tert-butyl4-hydroxyhydrocinnamoyloxy]-2-hydroxypropyl Methacrylate and
2-[3-(5-Phenylthio-2H-benzotriazol-2-yl)-5-tert-butyl4-hydroxyhydrocinnamoyloxy]-3-hydroxypropyl Methacrylate When the isomeric mixture of methacrylate monomers prepared in Example 18 is dissolved in toluene in the presence of 2,2'-azobis(isobutyronitrile) and heated to 80° C., the corresponding methacrylate copolymer named above is obtained.

EXAMPLE 25

A monomer composition comprising 23.5% butyl acrylate, 27% butyl methacrylate, 30% 2-hydroxyethyl acrylate, 15% styrene, 3% acrylic acid and 1.5% of the isomeric methacrylate monomer prepared in Example 18 (all values are by weight) and 0.4 phr of tert-amyl peroxy-O-(2-ethylhexyl) monoperoxy carbonate initiator is polymerized in refluxing xylene to form a stabilized acrylic polyol copolymer of moderate molecular weight.

EXAMPLE 26

When the acrylic polyol copolymer prepared in Example 25 is added to a standard acrylic-melamine formulation, a stabilized thermoset acrylic enamel having excellent resistance to degradation by actinic radiation and having excellent maintenance of 20 degree gloss values is obtained.

EXAMPLE 27

When the acrylic polyol copolymer prepared in Example 25 is added to a standard two component acrylic urethane refinish coating composition, a finish having excellent maintenance of 20 degree gloss values is obtained.

EXAMPLE 28

When the acrylic polyol copolymer prepared in Example 25 is added to a silver metallic acrylic alkyd enamel, an enamel having excellent maintenance of 60 degree gloss values is obtained.

What is claimed is:

1. A compound of formula I, II or III

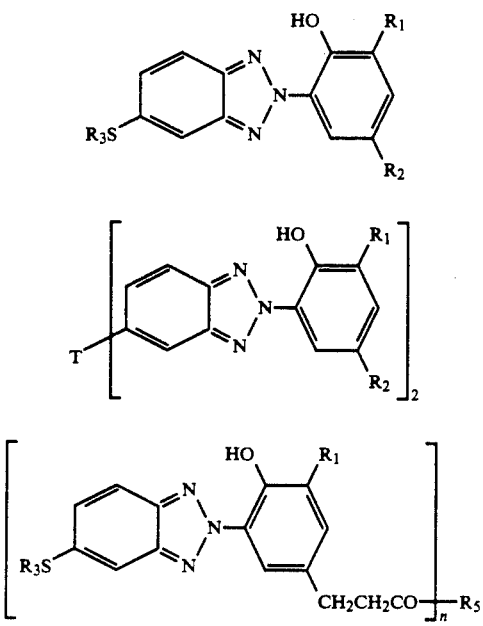

wherein
R₁ is hydrogen, straight or branched chain alkyl of 1 to 24 carbon atoms, cycloalkyl of 5 to 12 carbon atoms or phenylalkyl of 7 to 15 carbon atoms, R₂ is straight or branched chain alkyl of 1 to 24 carbon atoms, cycloalkyl of 5 to 12 carbon atoms or phenylalkyl of 7 to 15 carbon atoms; said alkyl substituted by one or more —OH, —OR₄ or —NH₂ groups where R₄ is alkyl of 1 to 12 carbon atoms; n is 1; R₅ is —OR₆ or —NH₂; R₆ is hydrogen or alkyl of 1 to 24 carbon atoms; or said alkyl substituted by one or more —OH groups; or —OR₆ is —(OCH₂CH₂)ᵥOH or —(OCH₂CH₂)ᵥOR₂₁ where w is 1 to 12 and R₂₁ is alkyl of 1 to 12 carbon atoms, R₃ is alkyl of 8 to 20 carbon atoms, alkenyl of 3 to 18 carbon atoms, cycloalkyl of 5 to 12 carbon atoms, phenylalkyl of 7 to 15 carbon atoms, aryl of 6 to 10 carbon atoms or said aryl substituted by one or two alkyl of 1 to 4 carbon atoms, and T is —S—, —S—S— or —S—E—S—,
where E is alkylene of 2 to 12 carbon atoms, cycloalkylene of 5 to 12 carbon atoms, or alkylene interrupted or terminated by cyclohexylene of 8 to 12 carbon atoms, and with the proviso that, when R₁ is sec-butyl and R₂ is tert-butyl, R₃ is not methyl.

2. A compound according to claim 1 wherein
R₁ is hydrogen, branched alkyl of 3 to 12 carbon atoms, cyclohexyl or phenylalkyl of 7 to 9 carbon atoms, R₂ is straight or branched chain alkyl of 1 to 12 carbon atoms, cyclohexyl or phenylalkyl of 7 to 9 carbon atoms;

R₃ is alkyl of 8 to 18 carbon atoms, allyl, cyclohexyl, phenylalkyl of 7 to 9 carbon atoms, phenyl or said phenyl substituted by one or two methyl groups, and T is —S— or —S—E—S,
where E is alkylene of 2 to 6 carbon atoms, cycloalkylene of 6 to 8 carbon atoms or alkylene terminated by cyclohexylene of 8 to 10 carbon atoms.

3. A compound according to claim 1 wherein
R₁ is hydrogen, branched alkyl of 4 to 8 carbon atoms, cyclohexyl, benzyl, α-methylbenzyl or α,α-dimethylbenzyl, R₂ is straight or branched chain alkyl of 1 to 8 carbon atoms, cyclohexyl, benzyl, α-methylbenzyl or α,α-dimethylbenzyl, R₃ is phenyl, and T is —S— or —S—E—S—,
where E is alkylene of 4 to 6 carbon atoms, cycloalkylene of 6 to 8 carbon atoms or dihydrolimonenediyl.

4. The compound according to claim 1 which is
(a)  5-n-dodecylthio-2-(2-hydroxy-3,5-di-tert-butylphenyl)-2H-benzotriazole;
(b)  5-phenylthio-2-(2-hydroxy-3,5-di-tert-butylphenyl)-2H-benzotriazole;
(c)  5-phenylthio-2-(2-hydroxy-5-methylphenyl)-2H-benzotriazole;
(d)  5-benzylthio-2-(2-hydroxy-3-tert-butyl-5-methylphenyl)-2H-benzotriazole;
(e)  5-phenylthio-2-(2-hydroxy-3-tert-butyl-5-methylphenyl)-2H-benzotriazole;
(f)  5-n-octylthio-2-(2-hydroxy-3,5-di-tert-butylphenyl)-2H-benzotriazole;
(g)  5-tridecylthio-2-(2-hydroxy-3,5-di-tert-butylphenyl)-2H-benzotriazole;
(h)  5,5'-(1,8-dithiaoctane-1,8-diyl)bis[2-(2-hydroxy-3,5-di-tert-butylphenyl)-2H-benzotriazole];
(i)  5,5'-(dithiadihydrolimonenediyl)bis[2-(2-hydroxy-3,5-di-tert-butylphenyl)-2H-benzotriazole];
(j)  5-phenylthio-2-(2-hydroxy-3,5-di-tert-octylphenyl)-2H-benzotriazole;
(k)  5-phenylthio-2-(2-hydroxy-3,5-di-α-cumylphenyl)-2H-benzotriazole;
(l)  5,5'-thiobis[2-(2-hydroxy-3,5-di-tert-butylphenyl)-2H-benzotriazole];
(m)  5-phenylthio-2-[2-hydroxy-3-tert-butyl-5-(β-carboxyethyl)phenyl]-2H-benzotriazole;
(n)  5-phenylthio-2-[2-hydroxy-3-tert-butyl-5-(β-octyloxycarbonylethyl)phenyl]-2H-benzotriazole;
(o)  5-phenylthio-2-{2-hydroxy-3-tert-butyl-5-[2-(ω-hydroxyocta(ethyleneoxy)-carbonylethyl]phenyl}-2H-benzotriazole;
(p)  5-phenylthio-2-[2-hydroxy-3-tert-butyl-5-(3-hydroxypropyl)phenyl]-2H-benzotriazole;
(q)  3-(5-phenylthio-2H-benzotriazol-2-yl)-5-tert-butyl-4-hydroxyhydrocinnamic acid;
(r)  3-(5-phenylthio-2H-benzotriazol-2-yl)-5-tert-butyl-4-hydroxyhydrocinnamamide;
(t)  ω-hydroxy-poly(ethyleneoxy) 3-(5-phenylthiobenzotriazol-2-yl)-5-tert-butyl-4-hydroxyhydrocinnamate; and
(u)  poly(ethyleneoxy) bis[3-(5-phenylthio-benzotriazol-2-yl)-5-tert-butyl-4-hydroxyhydrocinnamate].

* * * * *